US010329571B2

(12) United States Patent
Salunkhe et al.

(10) Patent No.: US 10,329,571 B2
(45) Date of Patent: Jun. 25, 2019

(54) DUAL CISTRONIC BACTERIAL EXPRESSION SYSTEM

(71) Applicant: Lupin Limited, Mumbai (IN)

(72) Inventors: Shardul Salunkhe, Pune (IN); Brajesh Varshney, Pune (IN); Sudheerbabu Soorapaneni, Pune (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 15/324,105

(22) PCT Filed: Jul. 9, 2015

(86) PCT No.: PCT/IB2015/055189
§ 371 (c)(1),
(2) Date: Jan. 5, 2017

(87) PCT Pub. No.: WO2016/005931
PCT Pub. Date: Jan. 14, 2016

(65) Prior Publication Data
US 2017/0159060 A1  Jun. 8, 2017

(30) Foreign Application Priority Data
Jul. 9, 2014 (IN) .......................... 2245/MUM/2014

(51) Int. Cl.
| C12N 15/70 | (2006.01) |
| C12N 15/67 | (2006.01) |
| C07K 14/27 | (2006.01) |
| C07K 14/605 | (2006.01) |
| C07K 16/22 | (2006.01) |
| C12N 9/52 | (2006.01) |
| C12P 21/02 | (2006.01) |

(52) U.S. Cl.
CPC ............. *C12N 15/70* (2013.01); *C07K 14/27* (2013.01); *C07K 14/605* (2013.01); *C07K 16/22* (2013.01); *C12N 9/52* (2013.01); *C12N 15/67* (2013.01); *C12P 21/02* (2013.01); *C12Y 304/24029* (2013.01); *C07K 2317/14* (2013.01); *C07K 2317/51* (2013.01); *C07K 2317/515* (2013.01); *C07K 2317/55* (2013.01); *C07K 2319/02* (2013.01); *C07K 2319/40* (2013.01)

(58) Field of Classification Search
None
See application file for complete search history.

(56) References Cited

U.S. PATENT DOCUMENTS

| 5,648,237 A | 7/1997 | Carter | |
| 8,853,380 B2 | 10/2014 | Salunkhe et al. | |
| 2015/0010529 A1* | 1/2015 | Wei ...................... | C12N 9/2408 424/94.62 |
| 2016/0017281 A1* | 1/2016 | Sunstrom ............... | C12N 15/85 435/69.4 |
| 2016/0289314 A1* | 10/2016 | Shandilya .............. | C07K 16/22 |

FOREIGN PATENT DOCUMENTS

| EP | 1356052 A2 * | 10/2003 | ............. C07K 16/00 |
| EP | 1356052 B1 | 8/2008 | |
| WO | 03018771 A2 | 3/2003 | |
| WO | WO-03018771 A2 * | 3/2003 | ............. C07K 16/00 |

OTHER PUBLICATIONS

Kim et al in "Two-Promoter Vector Is Highly Efficient for Over-production of Protein Complexes" (Protein Science, vol. 13, No. 6, Jun. 1, 2004, pp. 1698-1703 (Year: 2004).*
Banerjee et al "Over-expression of proteins using a modified pBAD24 vector in *E. coli* expression system" (Biotechnol Lett, 2009, pp. 1031-1036, vol. 31. (Year: 2009).*
Sletta et al Applied and Environ Microb Feb. 2007 pp. 906-912, vol. 73, No. 3 (Year: 2007).*
Bnerjee, S. et al., "Over-expression of proteins using a modified pBAD24 vector in *E. coli* expression system", Biotechnol. Lett, 2009, pp. 1031-1036, vol. 31.
Kim, K.-J. et al., "Two-promoter vector is highly efficient for overproduction of protein complexes", Protein Science, 2004, pp. 1698-1703, vol. 13.
Sletta, H. et al., "The Presence of N-Terminal Secretion Signal Sequences Leads to Strong Simulation of the Total Expression Levels of Three Tested Medically Important Proteins during High-Cell-Density Cultivations of *Escherichia coli*", Applied and Environmental Microbiology, Feb. 2007, pp. 906-912, vol. 73, No. 3.

* cited by examiner

*Primary Examiner* — Catherine S Hibbert
(74) *Attorney, Agent, or Firm* — The Webb Law Firm

(57) ABSTRACT

The present invention relates to the dual, independent cistron expression system in a single vector for the production of protein of interest proteins and peptides expressed as insoluble inclusion bodies formed in the bacteria *E. coli*. The present invention also provides the process for the expression of protein of interest using said bicistronic vector.

Figure 1:
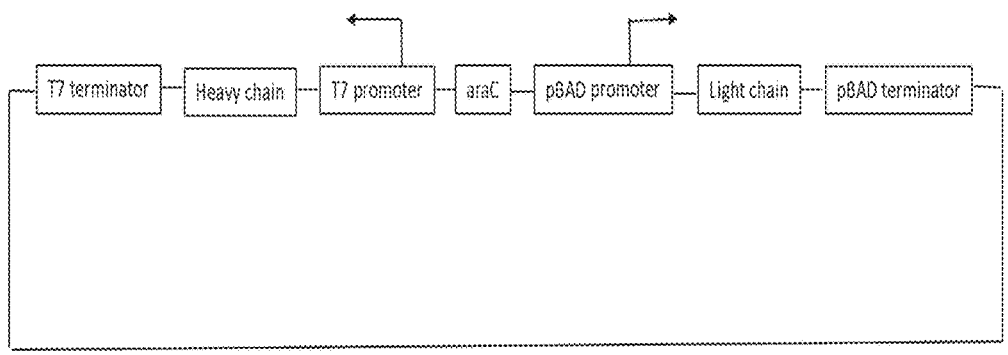

4 Claims, 7 Drawing Sheets
Specification includes a Sequence Listing.

| Lane. No | Lane description |
|---|---|
| 1 | Protein molecular weight marker |
| 2 | Light chain pBAD/BL21 A1 |
| 3 | Heavy chain pET21a/BL21A1 |
| 4 | Dual cistron clone pET21a-HC-LC /BL21 A1 |
| 5 | Ranibizumab standard |

| Lane. No | Lane description |
|---|---|
| 1 | Protein molecular weight marker |
| 2 | Dual cistron clone pET-ara-SAK-Lira /BL21 A1 |
| 3 | Single cistron clone pET-SAK-Lira |

DUAL CISTRONIC BACTERIAL EXPRESSION SYSTEM

CROSS-REFERENCE TO RELATED APPLICATIONS

This application is the United States national phase of International Application No. PCT/IB2015/055189 filed Jul. 9, 2015, and claims priority to Indian Patent Application No. 2245/MUM/2014 filed Jul. 9, 2014, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1606478_ST25.txt. The size of the text file is 28,005 bytes, and the text file was created on Jan. 4, 2017.

FIELD OF THE INVENTION

The present invention relates to the dual, independent cistron expression system in a single vector for the production of protein of interest comprises recombinant Fab fragments of antibodies or other antibody fragment, peptides and proteins expressed as insoluble inclusion bodies formed in the bacteria *E. coli*. The present invention also provides the process for the expression of protein of interest using said bicistronic vector.

BACKGROUND OF THE INVENTION

Recombinant DNA technology (rDNA) has revolutionized the way therapeutic agents are prepared. The required proteins are now made inside a foreign cell and purified. Proteins having post-translational modifications (PTMs) are generally expressed as recombinant molecules in mammalian or yeast system. The yeast expression systems like Pichia and Saccharomyces are closer to mammalian systems in terms of PTMs but still differ in the types of glycosylations like high mannose glycans in case of Pichia make them unsuitable for expression of recombinant proteins for human use.

Monoclonal antibodies (mAbs), antibodies, fusion proteins, Fab fragments of mAbs are used as therapeutic agents. The rDNA technology uses specialized vectors and expression systems for production of therapeutic proteins. The expression systems mainly consist of bacterial, yeast, insect or mammalian expression systems. Initially, most of the recombinant proteins were expressed in bacterial expression system using *E. coli* as host. There are several advantages of using *E. coli* as expression host such as ease of cloning, ease of expression, shorter timelines, shorter incubation periods and very high yields. Thus, proteins which do not need any PTMs can be safely expressed in *E. coli*.

Fabs, which are antigen binding fragment part of mAbs, need not to be expressed in mammalian systems as they do not contain glycosylation sites present in the Fc portion of the antibody. Hence, Fabs are usually expressed in *E. coli* system. During 1980-90s several researchers attempted the expression of Fabs in *E. coli*. PlückthunA.et. al., 1990*Behring Inst. Mitt.* (87):48-55are some of the earlier workers who reported secretion of Fab antibody from *E. coli*. Williamson R. A.et. al., 1991 *Biochem J.* 277 (Pt 2):561-3 reported use of bacteriophage lambda vectors for expression of Fab molecules in *E. coli*. Phage display system for production of Fab, bivalent antibody or chimeric antibody fragments in *E. coli*. Moreover, Fab was also produced in *E. coli* as misfolded, inclusion bodies and then refolded them to get the functional molecule and thereby 40% increase in the yields of antibody was obtained.

Most of the studies mentioned above used single promoter, i.e., phoA to drive the expression of both heavy and light chains. The ribosome binding site (rbs) present in between heavy and light chains drives the transcription and translation of second gene.

U.S. Pat. No. 5,648,237 also used similar single promoter (phoA) strategy to express Fabgenes in *E. coli*to get secreted product. The major drawback of the above strategy is that the expression levels of the second gene are usually lower than first gene, thus limiting the yields of the functional Fab.

Patent No. WO03018771 discloses a process for producing an antibody by two separate translational units, respectively encoding the light and heavy chains of said antibody or fragment, wherein both the chains are expressed in a sequential fashion, thereby specifically separating the production of the light and heavy chains and allowing the assembly of the light and heavy chains.

Patent No. EP1356052B1 discloses a method to produce full antibodies in prokaryotic cells. There is a presence of a first promoter and a first cistron to produce immunoglobulin light chain and a second promoter and a second cistron to produce immunoglobulin heavy chain, wherein both the chains are folded and assembled to form a biologically active immunoglobulin.

SUMMARY OF THE INVENTION

In an embodiment, the invention is related to a dual, independent cistron expression system in a single vector for the production of recombinant proteins and peptides expressed as insoluble inclusion bodies in bacterial cells.

In another embodiment, the invention is related to a process of preparation of dual, independent cistron expression system in a single vector having two different promoters for production of recombinant proteins and peptides expressed as insoluble inclusion bodies in bacterial cells.

In another embodiment, the invention is related to a dual, independent cistron expression system in a single vector having two different promoters for production of antibody fragments expressed as insoluble inclusion bodies in the bacterial cells.

In another embodiment, the invention is related to a dual, independent cistron expression system in a single vector having two different promoters for production of recombinant Fab fragment of antibodies expressed as insoluble inclusion bodies in the bacterial cells.

In another embodiment, the invention is related to a dual, independent cistron expression system in a single vector having two different promoters for production of recombinant peptides expressed as insoluble inclusion bodies in the bacterial cells.

In another embodiment the dual cistronic expression system comprises:
a) firstcistron comprising a promoter operably linked with polynucleotide sequence encoding protein of interest;
b) secondcistron comprising a promoter operably linked with polynucleotide sequence encoding protein of interest;
wherein the first and second cistrons are positioned in single vector and express a polynucleotide sequence encoding the protein of interest as inclusion bodies in bacterial cell.

In another embodiment the invention relates to dual cistronic vector comprising promoter operably linked to multiple cloning site contain gene of interest, ribosome binding site and terminator.

In yet another embodiment the invention relates to process for producing a protein of interest using dual cistronic expression system.

The details of one or more embodiments of the invention set forth below are illustrative in nature only and not intended to limit the scope of the invention. Other features, objects and advantages of the inventions will be apparent from the description.

BRIEF DESCRIPTION OF ACCOMPANYING FIGURES

FIG. 1; illustrates the formula of bicistronic vector

Figure 2:
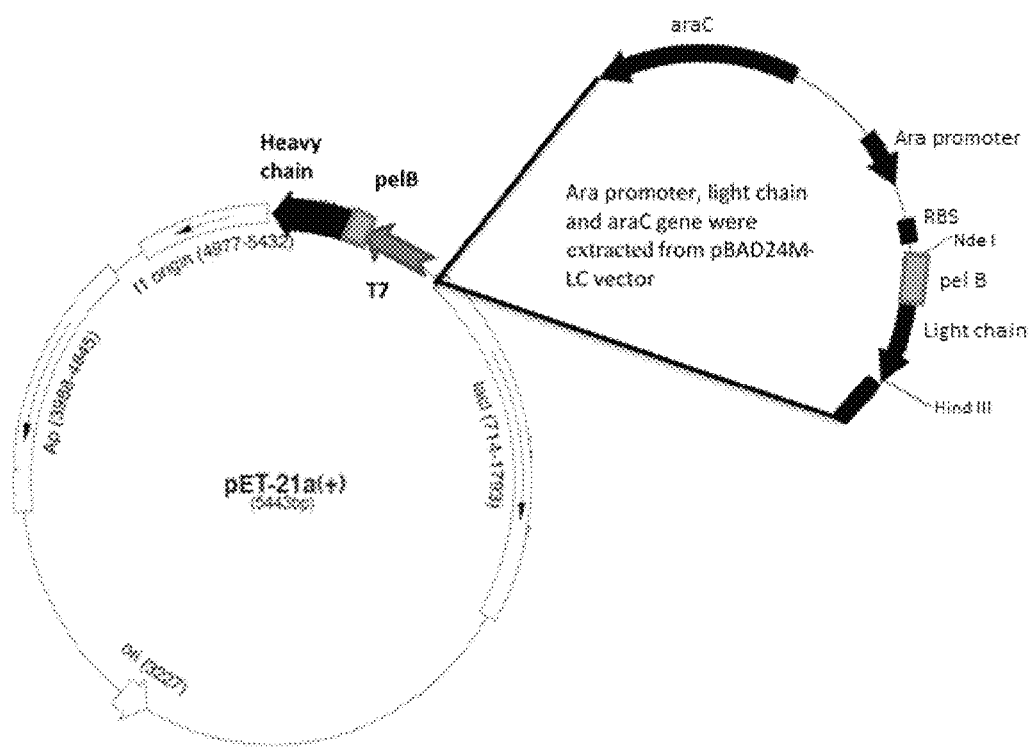

FIG. 2; illustrates the vector map of clone pET21a-HC-LC

Figure 3:
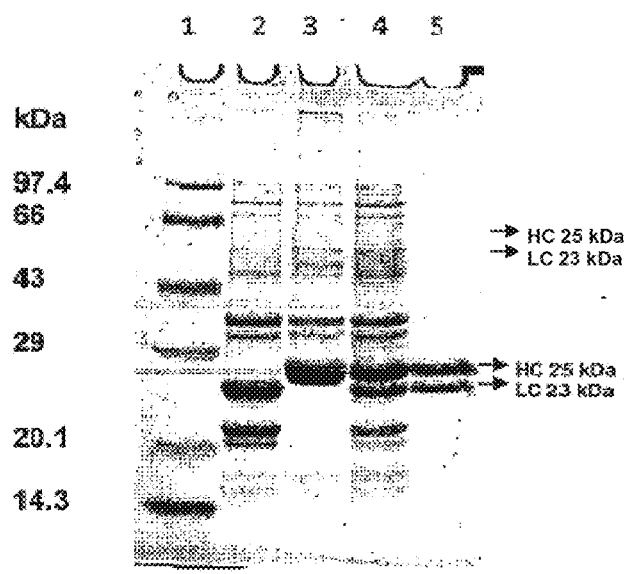
Figure 4:
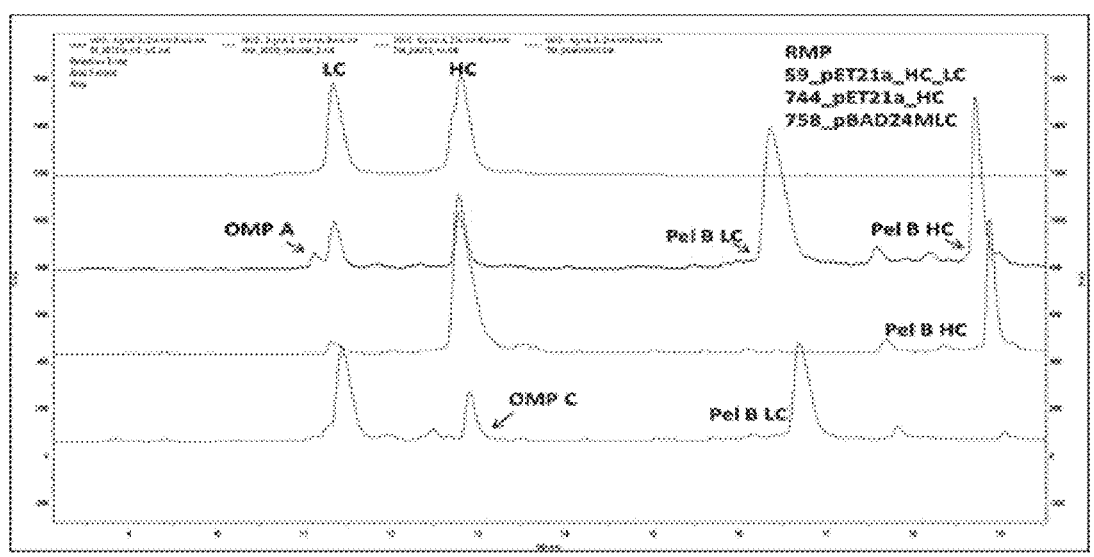
Figure 5:
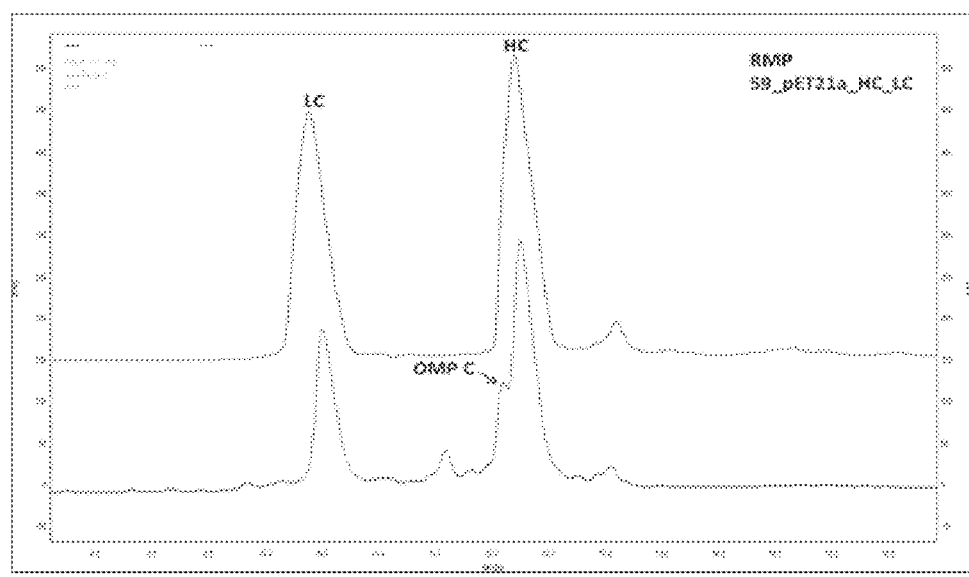
Figure 6:
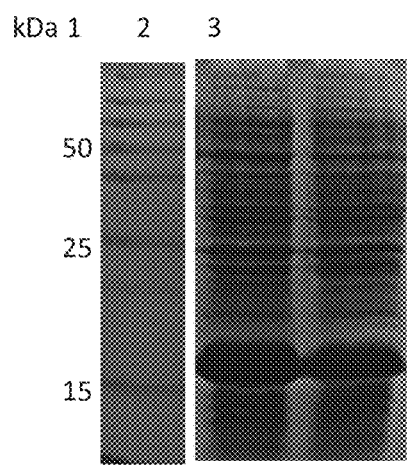

FIG. 3; illustrates the SDS PAGE analysis of insoluble pellet fraction of E. coli BL21A1 clone along with controls and the reference product FIG. 4; illustrates the RP-HPLC analysis of solubilized IB samples with LC and HC peaks seen in clone compared to reduced Fab molecule FIG. 5; illustrates the HPLC runs to seperate heavy chain peak from other proteins FIG. 6; illustrates significant increase in expression of SAK-Lira clone in dual cistron construct as compared with single cistron clone in E. coliBL21 A1 cell line.

Figure 7:
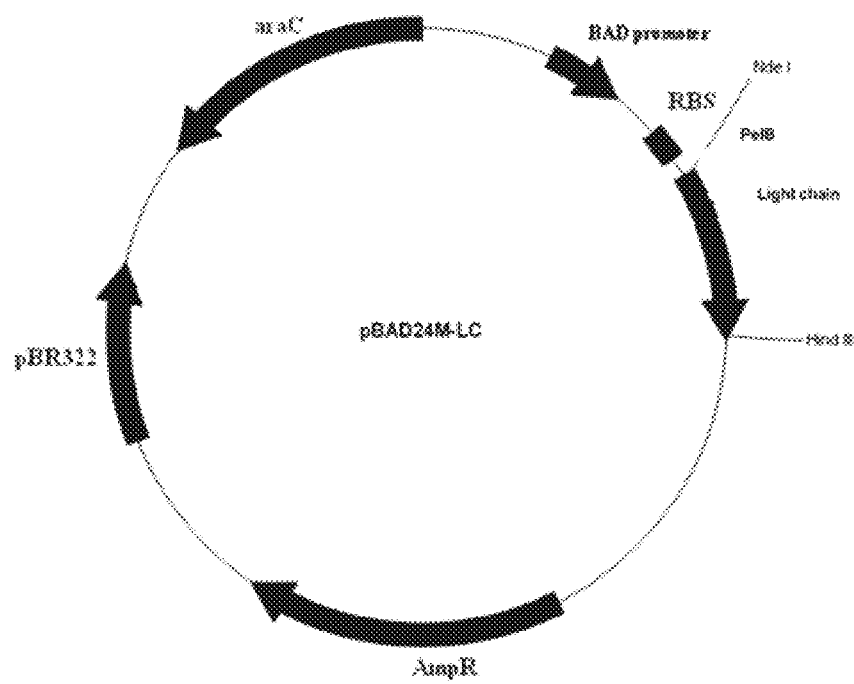

FIG. 7; illustrates the vector map pBAD24M-LC

DETAILED DESCRIPTION OF THE INVENTION

Definations:

As used herein, the term, "Protein of interest" refers herein to any polypeptide including protein and peptides used in biotherapeutic industry or for diagnostic or research purpose.

As used herein, the term "polynucleotide sequence encoding a protein of interest" as used herein includes DNA coding for a gene, preferably a heterologous gene expressing the polypeptide.

As used herein, the terms "recombinant protein and peptide" refers to a protein or peptide that is produced by the expression of recombinant DNA within living cells.

As used herein, the terms "Fab" and "antibody" are used interchangeably because antibody comprises two parts, i.e., Fab and Fc region.

As used herein, the term "vector" refers to a DNA molecule used as a vehicle to artificially carry foreign genetic material into bacterial cell, where it can be replicated and expressed.

As used herein, the term "cistron" refers to a section of DNA that contains the genetic code for a single polypeptide and functions as a hereditary unit.

As used herein, the term "dual independent cistron expression" refers to two separate cistrons which are used to express two same or different proteins independently.

As used herein, the term "same" is interchangable with identical or similar.

The term "Dual cistronic expression system" as used herein includes a polynucleotide sequence encoding a polypeptide to be expressed and sequences controlling its expression such as a promoter and optionally an enhancer sequence. The promoter of the invention is either operably linked to the gene to be expressed, i.e. transcription unit, or is separated therefrom by intervening DNA such as for example by the 5'-untranslated region of the heterologous gene. Preferably the expression system is flanked by one or more suitable restriction sites in order to enable the insertion of the expression cassette into a vector and/or its excision from a vector. Thus, the expression system according to the present invention may be used for the construction of an expression vector, in particular a bacterial expression vector.

As used herein, the term "promoters" refers to a regulatory region of DNA usually located upstream of a gene, providing a control point for regulated gene transcription.

As used herein, the terms "operably linked" refer to a functional relationship between two or more DNA segments, in particular gene sequences to be expressed and those sequences controlling their expression.

As used herein, the term "small peptides" or "peptides" refers to peptides ranging from 2 to 10 kDa used in biotherapeutic industry and diagnostic and research purposes like Liraglutide, exanetide, PTH, etc.

The present invention provides a dual cistronic expression system for the production of variety of recombinant protein of interest. In certain embodiment the dual cistronic expression system comprises two cistrons having promoter operably linked with polynucleotide sequence encoding protein of interest and terminator.

In certain embodiment the dual cistronic expression system comprises two cistrons express polynucleotide sequence encoding protein of interest are positioned in single vector.

In an embodiment the dual cistronic expression system comprises;
  a) firstcistron comprising a promoter operably linked with polynucleotide sequence encoding protein of interest;
  b) secondcistron comprising a promoter operably linked with polynucleotide sequence encoding protein of interest;
  wherein the first and second cistrons are positioned in single vector and express a polynucleotide sequence encoding the protein of interest as inclusion bodies formed in host cell.

In an embodiment the promoter may be selected from T7 promoter, arabinose promoter phoA, tac, lpp, lac-lpp, lac, trp, trc, preferably T7 promoter and arabinose promoter. In certain embodiment the dual cistronic expression system comprises two cistrons express polynucleotide sequence encoding protein of interest under the control of two promoters. In one embodiment both promoters control the expression of polynucleotide sequence encoding the same protein of interest. In another embodiment both promoters control the expression of polynucleotide sequence encoding protein of interest different in length of amino acid or physio-chemical properties.

In certain embodiment the protein of interest may be selected from peptides and proteins.

In some embodiment the proteins may be expressed in bicistronic vector. The protein comprises antibody or fragment thereof. Antibody fragment may be expressed in bicistronicexpression system. The antibody fragment may be selected from Fab heavy chain and light chains of antibodies or other antibody fragments such as scFv, Diabodies, Triabodies, Tetrabodies, Bis-scFv, Minibodies Fab$_2$ (bispecific), Fab3 (trispecific). In preferred embodiment the bicistronic expression system express polynucleotide sequence encoding heavy chain and light chain of antibody which forms a Fab antibody. In such embodiment the Fab antibody shows affinity to VEGF receptor and said Fab antibody is Ranibizumab.

In another embodiment the protein may be selected from but not limiting to G-CSF, IFN, erythroprotein, insulin and its varients, PTH (1-84aa), FSH, LH, GH and Protein disulfide isomerase (PDI).

In some embodiment the peptides may be expressed in bicistronic vector. The peptides comprise amino acid sequence are selected from at least less than 40 amnio acid or preferably less than 31 amino acid or more preferably less than 10 amino acid. In certain embodiment the peptide molecular weight is selected from about 2 to about 10 kDa. The peptide maybe selected from but not limiting to GLP-1 peptide analoguessuch as Liraglutide or Exendinor GLP-2 peptide like teduglutide and PTH (1-34aa) and insulin. In another preferred embodiment the bicistronic expression system express polynucleotide sequence encoding GLP-1 agonist peptide. In such embodiment the GLP-1 peptide is Liraglutide.

In another embodiment both promoters independently control the expression of different protein of interest such as heavy chain or light chain of antibody which are different in length of amino acid and physio-chemical property.

In an embodiment the dual cistronic expression system comprises:
a) first cistron comprises T7 promoter operably linked with polynucleotide sequence encoding heavy chain of antibody;
b) secondcistron comprises arabinose promoter operably linked with polynucleotide sequence encoding light chain of antibody;
Wherein the first and second cistrons are positioned in single vector and express the heavy chain and light chain of the antibody as inclusion bodies formed in host cell.

In such embodiment the antibody heavy chain and light chain of antibody comprise the nucleotide sequence sequence ID nos. 1 and sequence ID nos. 2 or amino acid sequence sequence ID nos. 3 and sequence ID nos.4.In some embodiment the position of first and second cistron is interchangeable wherein the second cistron may be cloned in vector at the position of first cistron and first cistron may be positioned at second cistron. The heavy chain and light chain of antibody independently express as inclusion bodies and may be further treated to obtain Fab antibody which shows affinity to VEGF receptor and said Fab antibody is Ranibizumab.

In certain embodiment the heavy chain and light chain of antibody are optionally expressed in combination with signal peptide, preferably pelB. Signal peptide directs the expression of protein in periplasmic space of the host cell.

In embodiment, the dualcistronicexpression system in a single vector having two different promoters, arabinose and T7 promoters regulating the production of heavy and light chains of recombinant Fab fragments, respectively and both having a pelB tag produced as insoluble inclusion bodies in the periplasmic space of *E. coli*.

In certain embodiment the heavy chain or light chain of antibody is optionally expressed in combination with regulator, preferably AraC gene in order to further increase the expression of protein.

The dual cistronic expression system provides equimolar expression of protein of interest. Equimolar expression is highly desirable in order to obtain protein of interest in suitable quality and quantity. It depends over the ratio of heavy and light chain or the ratio of subunit of polypeptide cloned in to the vector. In certain embodiment the the heavy chain and light chain are cloned in suitable ratio comprises the heavy chain is at least equal or higher than light chain to obtain equimolar expression of heavy and light chain. The heavy chain and light chain are cloned in a ratio selected from 1:5:0.7 to 1:1 which includes 1:3:0.8, 1:2:0.9, 1:2:1 1:1.

In embodiment the dual cistronic expression system comprises nucleotide sequence as set forth in sequence ID nos 19.

In another embodiment the dual cistronic expression system comprising:
a) firstcistron comprises T7 promoter operably linked with polynucleotide sequence encoding peptide;
b) secondcistron comprises arabinose promoter operably linked with polynucleotide sequence encoding peptide; wherein the first and second cistrons are positioned in single vector and express the peptide as inclusion bodies formed in host cell.

In such embodiment, the peptide is a GLP-1 analogue comprise nucleotide sequence as set forth in sequence ID nos 6 encoding the GLP-1 agonist peptide which is Liraglutide having amino acid sequence of sequence ID nos. 7.

In certain embodiment the peptide may be optionally expressed with signal peptide or regulator/enhancer known to the skilled person.

In certain embodiment the peptide may be optionally expressed with fusion partner or fusion tag in order to prevent the degradation of peptide. The fusion partner comprises amino acid sequence from 30 amino acid to 300 amino acid. The fusion partner comprises amino acid sequence selected from about 50 amino acid, 100 amino acid, about 136 amino acid, about 175 amino acid, about 250 amino acid, 300 amino acid, preferably about 136 amino acid. Fusion tag may be selected from but not limiting to Histidine-tag, glutathione-s-transferase (GST), Maltose binding protein, NusA, thioredoxin (TRX), polyhistidine (HIS), small ubiquitin-like modifier (SUMO) and ubiquitin (Ub) and staphylokinase (SAK) gene. In preferred embodiment the fusion tag is SAK gene. The detail use of SAK gene as fusion tag with protein of interest is disclosed in U.S. Pat. No. 8,853,380 which is incorporated herein as reference.

In some embodiment the bicistronic expression system further comprises selection marker which is selected from ampicillin, kanamycine, preferably ampicillin.

In another embodiment the present invention provides a process for producing a protein of interest comprising the steps of:
(i) transforming the host cell with a single vector essentially consisting of dual cistronic expression system;
(ii) culturing the transformed cell in suitable medium to express protein of interest, wherein the first and second cistron expresses the protein of interest in inclusion bodies;
(iii) performing solubilization of the inclusion bodies;
(iv) performing refolding of the protein of interest.

In embodiment the bicistronic expression system is transfected in to the suitable bacterial host cell in order to express the protein of interest. The suitable bacterial host cell is *E. coli* in which the protein of interest is expressed in the form of inclusion bodies. Inclusion bodies are the insoluble substance formed in the periplasm or cytoplasm of *E.coli*. Inclusion bodies may be isolated, solubilized and protein of interest may be recovered in active form by the techniques well known in the art.

In an embodiment, Fab heavy and light chains of antibodies or other antibody fragments such as scFv, Diabodies, Triabodies, Tetrabodies, Bis-scFv, Minibodies Fab$_2$ (bispecific), Fab3 (trispecific)were expressed as insoluble inclusion bodies in the periplasmic space of *E. coli* by constructing two independent cistrons in a single vector having two different promoters, arabinose and T7 promoters. The two different promoters, i.e., T7 promoter and arabinose promoter helped in the expression of heavy and light chains of Fab molecule, respectively. The antibody heavy and light chains were produced as non-functional inclusion bodies in the bacterial cell, i.e, *E. coli* which are subsequently extracted, refolded and purified.

In an embodiment of the invention, the cistron comprises as such that each gene (heavy and light chain) would have its own promoter and terminator in a single vector. The heavy chain was cloned under the control of T7 promoter while light chain was cloned under the control of arabinose promoter. Both the chains were preceded by signal sequence pelB tag for obtaining the product in the periplasmic space of the bacterial membrane.

The advantage of the bicistronic expression system is that both arabinose and T7 being strong promoters, high expression of both light and heavy chains are obtained from a single fermentation run instead of separate fermentations with light and heavy chain clones. The dual-cistronexpression system makes it simpler to characterize and maintain a single cell bank instead of separate cell banks for light and heavy chain clones. Moreover, the inclusion bodies thus obtained are relatively pure when extracted from the periplasmic space of the bacterial cells. The high level of expression and much purer forms of the light and heavy chains obtained as inclusion bodies are relatively easier to fold into functional Fab ex vivo, thereby significantly increasing the yield of the product.

Another advantage of the system is that a protein of interest may be cloned and expressed under arabinose and T7 promoters and expression level of the protein may be increased significantly.

The examples disclosed below are only for illustrative purpose of the invention and are not intended to be limiting.

EXAMPLE 1

Cloning of Heavy Chain in pET21a Vector

The DNA sequence used for cloning of heavy and light chain of Fab fragments is given in sequence IDnos 1 and 2, respectively. The heavy chain insert was amplified from synthetic DNA using gene specific primers. Primers are designed according to methods well known in the art. The heavy chain PCR product was then digested with NdeI-HindIII enzymes and ligated to pET21a vector digested with the same enzymes. The clones were screened by colony PCR and confirmed by restriction analysis. The resultant clone was designated as pET21a-HC. The recombinant vector was introduced into BL21A1 cell line and checked for expression of heavy chain.

EXAMPLE 2

Cloning of Light Chain in pBAD24M Vector

The light chain insert was amplified from synthetic DNA using gene specific primers. Primers are designed according to methods well known in the art. The amplified light chain was digested with NdeI-HindIII enzymes and ligated to digested pBAD24M vector (available in the laboratory) at same sites. The clones were screened by colony PCR and confirmed by restriction analysis. The resultant clone was designated as pBAD24M-LC. The recombinant vector was introduced into BL21A1 cell line and checked for expression of light chain.

EXAMPLE 3

Construction of Two Independent Cistrons in Same Vector

Primers were designed to amplify light chain along with arabinose promoter, terminator and araCgene. Primers are designed according to methods well known in the art. The primers added BgIII linker to the amplified product. The pET21a vector had single BgIII site upstream of the T7 promoter. The light chain expression cassette was amplified from the template pBAD24M with the vector specific primers and cloned into pET21a-HC clone at BgIII site. The clone was confirmed by restriction digestion and sequencing. The final clone was designated as pET21a-HC-LC and suitable clone short listed based on expression. The clone map of the pET21a-HC-LC is presented in FIG. 2.

The clone thus generated contains all the segments required for independent regulation and expression of both heavy and light chains.

EXAMPLE 4

Expression Analysis

*E. coli*BL21 A1 cell line was used as expression host. Apart from BL21 A1, BL21 DE3 or any other cell line containing T7 promoter in the genome is used. BL21 A1 cells were transformed using the above selected clone along with pET21a-HC and pBAD24M-LC as controls. The Heavy chain was induced by IPTG while the light chain was induced by arabinose. The inducer concentration was 13 mM arabinose and 1 mM IPTG and the induction was done when the culture $OD_{600}$ was ~1. The cells were harvested 4 hr post induction. The study was done in shake flasks. The harvest obtained was bead lysed and centrifuged to separate soluble and insoluble fractions. The samples were loaded on 12% SDS PAGE gels to check the expression. The SDS PAGE gel analysis is shown in FIG. 3. Reduced ranibizumab was loaded in Lane 5 off FIG. 3 to confirm expression of reduced light and heavy chains.

The SDS PAGE analysis showed expression of both chains in the insoluble pellet fraction and the same was confirmed by RP-HPLC analysis wherein the retention times of light and heavy chains of the reference product corresponded to the retention times of the in-house product. The controls used were reduced Fab molecule (reference product), and products of pET21a-HC clone and pBAD24M clone. Thus, the expression of both the heavy and the light chain from a single clone was confirmed. The RP-HPLC analysis is shown in FIGS. 4 and 5. In RP-HPLC, solubilized and reduced IBs of the dual cistron clone were compared with reduced ranibizumab (RMP) and clones separately expressing heavy and light chains i.e. pET21-HC and pBAD24MLC.

The retention time (RT) of principal peak of solubilized IB of pBAD24MLC expressing only light chain matches with the RT of light chain of reduced RMP. An impurity peak at RT 13 mins matches the retention time of heavy chain, which was indicative of similar hydrophobicity. The impurities therefore were characterized by LC-MS/MS and were finally annotated as host cell protein OMP C and light chain with uncleaved leader sequence at RT 17 mins. The heavy chain expressed by pET21a-HC matches with the reference standard heavy chain. The profile also indicated a post peak at RT 19 mins which was characterized as heavy chain with uncleaved leader sequence. The dual cistronic clone pET21 a_HC_LC that expresses both LC and HC have 2 main peaks that have equivalent retention times as that of the LC and HC of reference standard. But, since the OMP C co-eluted with heavy chain, the reversed phase method of testing had to be resolved better and this is presented in the FIG. 4.

The existing method on Zorbax C8 RP column was modified to Aeriswidepore C8 and the co-eluting species were resolved. The solubilized IB of pET2 1 a_HC_LC on Aeriswidepore C8 exhibited a distinct LC, HC and OMP C peaks enabling the identity and precise quantification of individual subunits in IB as evident in FIG. 5.

Although certain embodiments and examples have been described in detail above, those having ordinary skill in the art will clearly understand that many modifications are possible in the embodiments and examples without departing from the teachings thereof.

EXAMPLE NO 5

Cloning of Small Peptide (Liraglutide) with Staphylokinase (SAK) Fusion Tag in pET24a Vector The SAK and Liraglutide genes were amplified from synthetic DNA using gene specific primers. Primers are designed according to methods well known in the art and PCR products were digested with NdeI-BamHI and BamHI-HindIII enzymes and ligated to digested pET24a vector at NdeI-HindIII sites. The clones were screened by colony PCR and confirmed by restriction analysis. The resultant clone was designated as pET24a-SAK-Lira.

EXAMPLE 6

Cloning of Small Peptide (Liraglutide) with Staphylokinase Fusion Tag in pBAD24M Vector As given in example no 6, Liraglutide with SAK tag was cloned into pBAD24M vector. The clone was designated as pBAD24M-SAK-Lira.

EXAMPLE NO 7

Construction of Two Independent Cistrons in Same Vector with Both Cistrons Expressing SAK-Lira Fusion Peptide The clone design strategy used in example no. 3 was used to construct dual cistron clone of Liraglutide, wherein SAK-Lira fusion gene along with arabinose expression cassette was amplifed from pBAD24M-SAK-Lira clone and cloned into pET24a-SAK-Lira clone to construct dual cistron construct. The clone was labelled as pET-ara-SAK-Lira

EXAMPLE NO 8

Expression Analysis of Dual Cistron Clone with SAK-Lira Fusion Protein

*E. coli* BL21 A1 cell line was used as expression host. Apart from BL21 A1, BL21 DE3 or any other cell line containing T7 promoter in genome is used. BL21 A1 cells were transformed using the above single and dual cistron constructs. The clones were induced by IPTG and arabinose. The inducer concentration was 13 mM arabinose and 1 mM IPTG and the induction was done when the culture $OD_{600}$ was ~1. The cells were harvested 4 hr post induction. The study was done in shake flasks. The harvest obtained was bead lysed and centrifuged to separate soluble and insoluble fractions. The samples were loaded on 12% SDS PAGE gels to check the expression.

The SDS PAGE gel analysis clearly shows increased expression of SAK-Lira fusion protein in dual cistron clone (FIG. 6 lane 2) as compared with single cistron pET24a-SAK-Lira clone (FIG. 6 Lane 3).

---

The invention claimed is:

1. A process for producing an antibody or fragment thereof comprising the steps of:
   (i) transforming a bacterial host cell with a single vector consisting of a dual cistronic expressions system comprising:
      a) a first cistron comprising a T7 promoter operably linked with a polynucleotide sequence encoding a heavy chain of an antibody or fragment thereof; and
      b) a second cistron comprising an arabinose promoter operably linked with a polynucleotide sequence encoding a light chain of an antibody or fragment thereof;
   (ii) culturing the transformed bacterial host cell in a suitable medium to simultaneously express the heavy and the light chains of the antibody or the fragment thereof, wherein the heavy and light chains are expressed at equimolar levels as inclusion bodies; and
   (iii) subjecting the inclusion bodies to a solubilization and refolding step to obtain a functional antibody or fragment thereof,
   wherein the recombinant dual cistronic vector encoding the light and heavy chains comprises the polynucleotide sequence set forth in SEQ ID NO: 19.

2. The process of claim 1, wherein the antibody fragment is Ranibizumab.

3. The process of claim 1, wherein the bacterial host cell is *E. coli*.

4. A process for producing Ranibizumab comprising the steps of:
   (i) transforming an *E. coli* host cell with a recombinant dual cistronic vector comprising SEQ ID NO: 19;
   (ii) culturing the transformed *E. coli* host cell in a suitable medium to express the heavy and light chains of Ranibizumab in inclusion bodies at equimolar levels; and
   (iii) subjecting the inclusion bodies to a solubilizing and refolding step to obtain a functional Ranibizumab.

* * * * *

SEQUENCE LISTING

```
<160> NUMBER OF SEQ ID NOS: 19

<210> SEQ ID NO 1
<211> LENGTH: 762
<212> TYPE: DNA
<213> ORGANISM: artificial
<220> FEATURE:
<223> OTHER INFORMATION: Ranibizumab heavy chain sequence

<400> SEQUENCE: 1
atgaaatacc tgctgccgac agctgctgct ggtctgctgc tcctcgctgc ccagccggcg     60
atggccgaag tccaactggt cgaatcgggt ggtggtctgg tccaaccggg tggctctctg    120
cgtctgtcgt gtgctgcctc gggctatgat tttacccatt atggtatgaa ctgggtccgt    180
caggccccgg gtaaaggtct ggaatgggtg ggctggatta atacctacac gggtgaaccg    240
acctatgcgg ccgattttaa acgtcgcttt acgttctctc tggacacctc gaagagcacg    300
gcatatctgc agatgaacag tctgcgcgcg gaagataccg ccgtgtatta ctgcgcgaag    360
tacccgtatt actatggcac gtcccactgg tattttgacg tttggggcca aggtaccctg    420
gtcaccgtga gcagcgcgag caccaaaggc ccgagcgtgt tcccgctggc cccgagttcc    480
aagtctacca gtggcggtac ggcagctctg ggttgtctgg ttaaagatta ttttccgaa     540 ccggttaccg tctcctggaa cagcggcgca ctgacctctg gtgtgcatac gttcccggct    600
```

-continued

```
gttctgcagt catcgggcct gtacagcctg agcagcgtgg ttaccgttcc gagttcctca    660
ctgggtaccc aaacgtatat ctgcaacgtc aatcacaaac cgagcaatac caaagtggac    720
aaaaaagtgg aaccgaaatc gtgtgataaa acgcatctgt aa                       762
```

<210> SEQ ID NO 2
<211> LENGTH: 711
<212> TYPE: DNA
<213> ORGANISM: artificial
<220> FEATURE:
<223> OTHER INFORMATION: Ranibizumab Light chain: 2295-3005Nt seq

<400> SEQUENCE: 2

```
atgaaatacc tgctgccgac agctgctgct ggtctgctgc tcctcgctgc ccagccggcg     60
atggccgaca ttcaactgac gcaaagtccg agcagcctga gcgcatccgt gggcgaccgt    120
gtgacgatta cctgttccgc aagccaagac atctctaact atctgaattg gtaccagcaa    180
aaaccgggca aggcaccgaa agtcctgatt tattttacca gctctctgca ttccggcgtt    240
ccgtcacgtt ttagcggctc tggtagtggc accgatttca ccctgacgat cagttccctg    300
cagccggaag actttgctac gtattactgc cagcaataca gcaccgtgcc gtggacgttc    360
ggtcagggca ccaaggttga aattaaacgt acggttgcgg ccccgtctgt ctttatcttc    420
ccgccgagtg atgaacagct gaaatcgggt accgcaagcg tggtttgtct gctgaacaat    480
ttctatcccg cgaagcaaa ggtccagtgg aaagtggaca cgctctgca gtccggcaat    540
tcacaagaat cggtgaccga acaagatagc aaggactcta cgtacagtct gtcatcgacc    600
ctgacgctgt ccaaagcgga ttatgaaaaa cacaaggttt acgcctgcga agtcacccat    660
caaggtctgt cgtctccggt taccaagagt ttcaatcgtg gcgaatgtta a             711
```

<210> SEQ ID NO 3
<211> LENGTH: 253
<212> TYPE: PRT
<213> ORGANISM: artificial
<220> FEATURE:
<223> OTHER INFORMATION: Ranibizumab heavy chain amino acid sequence

<400> SEQUENCE: 3

```
Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Tyr Asp Phe Thr His Tyr Gly Met Asn Trp Val Arg Gln Ala Pro Gly
    50                  55                  60

Lys Gly Leu Glu Trp Val Gly Trp Ile Asn Thr Tyr Thr Gly Glu Pro
65                  70                  75                  80

Thr Tyr Ala Ala Asp Phe Lys Arg Arg Phe Thr Phe Ser Leu Asp Thr
                85                  90                  95

Ser Lys Ser Thr Ala Tyr Leu Gln Met Asn Ser Leu Arg Ala Glu Asp
            100                 105                 110

Thr Ala Val Tyr Tyr Cys Ala Lys Tyr Pro Tyr Tyr Gly Thr Ser
        115                 120                 125

His Trp Tyr Phe Asp Val Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160
```

```
Lys Ser Thr Ser Gly Gly Thr Ala Ala Leu Gly Cys Leu Val Lys Asp
            165                 170                 175

Tyr Phe Pro Glu Pro Val Thr Val Ser Trp Asn Ser Gly Ala Leu Thr
        180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Leu
            245                 250
```

<210> SEQ ID NO 4
<211> LENGTH: 236
<212> TYPE: PRT
<213> ORGANISM: artificial
<220> FEATURE:
<223> OTHER INFORMATION: Ranibizumab Light chain Amino acid sequence

<400> SEQUENCE: 4

```
Met Lys Tyr Leu Leu Pro Thr Ala Ala Gly Leu Leu Leu Leu Ala
1               5                   10                  15

Ala Gln Pro Ala Met Ala Asp Ile Gln Leu Thr Gln Ser Pro Ser Ser
            20                  25                  30

Leu Ser Ala Ser Val Gly Asp Arg Val Thr Ile Thr Cys Ser Ala Ser
        35                  40                  45

Gln Asp Ile Ser Asn Tyr Leu Asn Trp Tyr Gln Gln Lys Pro Gly Lys
50                  55                  60

Ala Pro Lys Val Leu Ile Tyr Phe Thr Ser Ser Leu His Ser Gly Val
65                  70                  75                  80

Pro Ser Arg Phe Ser Gly Ser Gly Ser Gly Thr Asp Phe Thr Leu Thr
            85                  90                  95

Ile Ser Ser Leu Gln Pro Glu Asp Phe Ala Thr Tyr Tyr Cys Gln Gln
        100                 105                 110

Tyr Ser Thr Val Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

<210> SEQ ID NO 5
<211> LENGTH: 762
<212> TYPE: DNA
<213> ORGANISM: artificial

<220> FEATURE:
<223> OTHER INFORMATION: Heavy chain 940-178 complement

<400> SEQUENCE: 5

```
ttacagatgc gttttatcac acgatttcgg ttccactttt ttgtccactt tggtattgct      60
cggtttgtga ttgacgttgc agatatacgt ttgggtaccc agtgaggaac tcggaacggt     120
aaccacgctg ctcaggctgt acaggcccga tgactgcaga acagccggga acgtatgcac     180
accagaggtc agtgcgccgc tgttccagga cggtaaccgg ttccggaaa ataatctttt     240
aaccagacaa cccagagctg ccgtaccgcc actggtagac ttggaactcg gggccagcgg     300
gaacacgctc gggcctttgg tgctcgcgct gctcacggtg accagggtac cttggcccca     360
aacgtcaaaa taccagtggg acgtgccata gtaatacggg tacttcgcgc agtaatacac     420
ggcggtatct tccgcgcgca gactgttcat ctgcagatat gccgtgctct tcgaggtgtc     480
cagagagaac gtaaagcgac gtttaaaatc ggccgcatag gtcggttcac ccgtgtaggt     540
attaatccag cccacccatt ccagaccttt acccggggcc tgacggaccc agttcatacc     600
ataatgggta aaatcatagc ccgaggcagc acacgacaga cgcagagagc cacccggttg     660
gaccagacca ccacccgatt cgaccagttg gacttcggcc atcgccggct gggcagcgag     720
gagcagcaga ccagcagcag ctgtcggcag caggtatttc at                        762
```

<210> SEQ ID NO 6
<211> LENGTH: 96
<212> TYPE: DNA
<213> ORGANISM: artificial
<220> FEATURE:
<223> OTHER INFORMATION: DNA sequence of Liraglutide

<400> SEQUENCE: 6

```
catgcagaag gcacctttac gagtgatgtg agctcttatc tggaaggcca ggcggccaaa      60
gaatttattg cgtggctggt tcgtggccgt ggttaa                                96
```

<210> SEQ ID NO 7
<211> LENGTH: 31
<212> TYPE: PRT
<213> ORGANISM: artificial
<220> FEATURE:
<223> OTHER INFORMATION: Amino acid sequence of Liraglutide

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 8
<211> LENGTH: 456
<212> TYPE: DNA
<213> ORGANISM: artificial
<220> FEATURE:
<223> OTHER INFORMATION: SAK nucleotide sequence (with EK site)

<400> SEQUENCE: 8

```
catatgtcaa gttcattcga caaaggaaaa tataaaaaag gcgatgacgc gagttatttt      60
gaaccaacag gcccgtattt gatggtaaat gtgactggag ttgatggtaa aggaaatgaa     120
ttgctatccc ctcattatgt cgagtttcct attaaacctg gactacact tacaaaagaa     180
aaaattgaat acctgcagga tgatgatgat aaatacgtag aatgggcatt agatgcgaca     240
```

```
gcatataaag agtttagagt agttgaatta gatccaagcg caaagatcga agtcacttat    300
tatgataaga ataagaaaaa agaagaaacg aagtctttcc ctataacaga aaaaggtttt    360
gttgtcccag atttatcaga gcatattaaa aaccctggat tcaacttaat tacaaaggtt    420
gttatagaaa agaaaggatc cgatgatgat gataaa                              456
```

```
<210> SEQ ID NO 9
<211> LENGTH: 151
<212> TYPE: PRT
<213> ORGANISM: artificial
<220> FEATURE:
<223> OTHER INFORMATION: SAK amino acid sequence (with EK tag)

<400> SEQUENCE: 9
```

Met Ser Ser Ser Phe Asp Lys Gly Lys Tyr Lys Lys Gly Asp Asp Ala
1               5                   10                  15

Ser Tyr Phe Glu Pro Thr Gly Pro Tyr Leu Met Val Asn Val Thr Gly
            20                  25                  30

Val Asp Gly Lys Gly Asn Glu Leu Leu Ser Pro His Tyr Val Glu Phe
        35                  40                  45

Pro Ile Lys Pro Gly Thr Thr Leu Thr Lys Glu Lys Ile Glu Tyr Leu
    50                  55                  60

Gln Asp Asp Asp Lys Tyr Val Glu Trp Ala Leu Asp Ala Thr Ala
65                  70                  75                  80

Tyr Lys Glu Phe Arg Val Val Glu Leu Asp Pro Ser Ala Lys Ile Glu
                85                  90                  95

Val Thr Tyr Tyr Asp Lys Asn Lys Lys Glu Glu Thr Lys Ser Phe
            100                 105                 110

Pro Ile Thr Glu Lys Gly Phe Val Val Pro Asp Leu Ser Glu His Ile
        115                 120                 125

Lys Asn Pro Gly Phe Asn Leu Ile Thr Lys Val Val Ile Glu Lys Lys
    130                 135                 140

Gly Ser Asp Asp Asp Asp Lys
145                 150

```
<210> SEQ ID NO 10
<211> LENGTH: 17
<212> TYPE: DNA
<213> ORGANISM: artificial
<220> FEATURE:
<223> OTHER INFORMATION: T7 promoter: 1011-1027

<400> SEQUENCE: 10
ctatagtgag tcgtatt                                                   17

<210> SEQ ID NO 11
<211> LENGTH: 52
<212> TYPE: DNA
<213> ORGANISM: artificial
<220> FEATURE:
<223> OTHER INFORMATION: T7 terminator:26-72

<400> SEQUENCE: 11
ttcagcaaaa aacccctcaa gacccgttta gaggccccaa ggggttatgc ta            52

<210> SEQ ID NO 12
<211> LENGTH: 10
<212> TYPE: DNA
<213> ORGANISM: artificial
<220> FEATURE:
<223> OTHER INFORMATION: RBS of pET21a: 947-957
```

```
<400> SEQUENCE: 12
tctccttctt                                                                10

<210> SEQ ID NO 13
<211> LENGTH: 879
<212> TYPE: DNA
<213> ORGANISM: artificial
<220> FEATURE:
<223> OTHER INFORMATION: AraC gene: 1048-1927

<400> SEQUENCE: 13
ttatgacaac ttgacggcta catcattcac ttttctttca caaccggcac ggaactcgct        60
cgggctggcc ccggtgcatt ttttaaatac ccgcgagaaa tagagttgat cgtcaaaacc       120
aacattgcga ccgacggtgg cgataggcat ccgggtggtg ctcaaaagca gcttcgcctg       180
gctgatacgt tggtcctcgc gccagcttaa gacgctaatc cctaactgct ggcggaaaag       240
atgtgacaga cgcgacggcg acaagcaaac atgctgtgcg acgctggcga tatcaaaatt       300
gctgtctgcc aggtgatcgc tgatgtactg acaagcctcg cgtacccgat tatccatcgg       360
tggatggagc gactcgttaa tcgcttccat gcgccgcagt aacaattgct caagcagatt       420
tatcgccagc agctccgaat agcgcccttc cccttgcccg gcgttaatga tttgcccaaa       480
caggtcgctg aaatgcggct ggtgcgcttc atccgggcga agaacccccg tattggcaaa       540
tattgacggc cagttaagcc attcatgcca gtaggcgcgc ggacgaaagt aaacccactg       600
gtgataccat tcgcgagcct ccggatgacg accgtagtga tgaatctctc ctggcgggaa       660
cagcaaaata tcacccggtc ggcaaacaaa ttctcgtccc tgattttttca ccacccccctg      720 accgcgaatg gtgagattga aatataaccc tttcattccc agcggtcggt cgataaaaaa       780
atcgagataa ccgttggcct caatcggcgt taaacccgcc accagatggg cattaaacga       840
gtatcccggc agcaggggat cattttgcgc ttcagccat                              879

<210> SEQ ID NO 14
<211> LENGTH: 27
<212> TYPE: DNA
<213> ORGANISM: artificial
<220> FEATURE:
<223> OTHER INFORMATION: Arabinose promoter: 2203-2230

<400> SEQUENCE: 14
acgcttttta tcgcaactct ctactgt                                            27

<210> SEQ ID NO 15
<211> LENGTH: 425
<212> TYPE: DNA
<213> ORGANISM: artificial
<220> FEATURE:
<223> OTHER INFORMATION: Arabinose terminator: 3011-3438

<400> SEQUENCE: 15
gctgttttgg cggatgagag aagattttca gcctgataca gattaaatca gaacgcagaa        60
gcggtctgat aaaacagaat ttgcctggcg gcagtagcgc ggtggtccca cctgacccca       120
tgccgaactc agaagtgaaa cgccgtagcg ccgatggtag tgtggggtct ccccatgcga       180
gagtagggaa ctgccaggca tcaaataaaa cgaaaggctc agtcgaaaga ctgggccttt       240
cgttttatct gttgtttgtc ggtgaacgct ctcctgagta ggacaaatcc gccgggagcg       300
gatttgaacg ttgcgaagca acggcccgga gggtggcggg caggacgccc gccataaact       360
```

```
gccaggcatc aaattaagca gaaggccatc ctgacggatg gccttttttgc gtttctacaa    420 actct                                                                 425
```

```
<210> SEQ ID NO 16
<211> LENGTH: 1084
<212> TYPE: DNA
<213> ORGANISM: artificial
<220> FEATURE:
<223> OTHER INFORMATION: LacI sequence: 3810-4890

<400> SEQUENCE: 16
tgtgaaacca gtaacgttat acgatgtcgc agagtatgcc ggtgtctctt atcagaccgt      60
ttcccgcgtg gtgaaccagg ccagccacgt ttctgcgaaa acgcgggaaa aagtggaagc     120
ggcgatggcg gagctgaatt acattcccaa ccgcgtggca caacaactgg cgggcaaaca     180
gtcgttgctg attggcgttg ccacctccag tctggccctg cacgcgccgt cgcaaattgt     240
cgcggcgatt aaatctcgcg ccgatcaact gggtgccagc gtggtggtgt cgatggtaga     300
acgaagcggc gtcgaagcct gtaaagcggc ggtgcacaat cttctcgcgc aacgcgtcag     360
tgggctgatc attaactatc cgctggatga ccaggatgcc attgctgtgg aagctgcctg     420
cactaatgtt ccggcgttat ttcttgatgt ctctgaccag acacccatca acagtattat     480
tttctcccat gaagacggta cgcgactggg cgtggagcat ctggtcgcat tgggtcacca     540
gcaaatcgcg ctgttagcgg cccattaag ttctgtctcg gcgcgtctgc gtctggctgg     600
ctggcataaa tatctcactc gcaatcaaat tcagccgata gcggaacggg aaggcgactg     660
gagtgccatg tccggttttc aacaaaccat gcaaatgctg aatgagggca tcgttcccac     720
tgcgatgctg gttgccaacg atcagatggc gctgggcgca atgcgcgcca ttaccgagtc     780
cgggctgcgc gttggtgcgg atatctcggt agtgggatac gacgataccg aagacagctc     840
atgttatatc ccgccgttaa ccaccatcaa acaggatttt cgcctgctgg ggcaaaccag     900
cgtggaccgc ttgctgcaac tctctcaggg ccaggcggtg aagggcaatc agctgttgcc     960
cgtctcactg gtgaaaagaa aaaccaccct ggcgcccaat acgcaaaccg cctctccccg    1020
cgcgttggcc gattcattaa tgcagctggc acgacaggtt tcccgactgg aaagcgggca    1080
gtga                                                                1084
```

```
<210> SEQ ID NO 17
<211> LENGTH: 861
<212> TYPE: DNA
<213> ORGANISM: artificial
<220> FEATURE:
<223> OTHER INFORMATION: bla (ampicillin resistance): 7085-7942

<400> SEQUENCE: 17
ttaccaatgc ttaatcagtg aggcacctat ctcagcgatc tgtctatttc gttcatccat      60
agttgcctga ctccccgtcg tgtagataac tacgataggg gagggcttac catctggccc     120
cagtgctgca atgataccgc gagacccacg ctcaccggct ccagatttat cagcaataaa     180
ccagccagcc ggaagggccg agcgcagaag tggtcctgca actttatccg cctccatcca     240
gtctattaat tgttgccggg aagctagagt aagtagttcg ccagttaata gtttgcgcaa     300
cgttgttgcc attgctgcag gcatcgtggt gtcacgctcg tcgtttggta tggcttcatt     360
cagctccggt tcccaacgat caaggcgagt tacatgatcc cccatgttgt gcaaaaaagc     420
ggttagctcc ttcggtcctc cgatcgttgt cagaagtaag ttggccgcag tgttatcact     480
catggttatg gcagcactgc ataattctct tactgtcatg ccatccgtaa gatgcttttc     540
```

-continued

```
tgtgactggt gagtactcaa ccaagtcatt ctgagaatag tgtatgcggc gaccgagttg    600 ctccttgcccg gcgtcaatac gggataatac cgcgccacat agcagaactt taaaagtgct    660
catcattgga aaacgttctt cggggcgaaa actctcaagg atcttaccgc tgttgagatc    720
cagttcgatg taacccactc gtgcacccaa ctgatcttca gcatctttta ctttcaccag    780
cgtttctggg tgagcaaaaa caggaaggca aaatgccgca aaaagggaa taagggcgac     840 acggaaatgt tgaatactca t                                              861
```

<210> SEQ ID NO 18
<211> LENGTH: 1
<212> TYPE: DNA
<213> ORGANISM: artificial
<220> FEATURE:
<223> OTHER INFORMATION: pBR322 origin 6323 sequence

<400> SEQUENCE: 18

```
t                                                                    1
```

<210> SEQ ID NO 19
<211> LENGTH: 8540
<212> TYPE: DNA
<213> ORGANISM: artificial
<220> FEATURE:
<223> OTHER INFORMATION: Complete clone sequence of dual cistron vector
      including heavy and light chainfab

<400> SEQUENCE: 19

```
atccggatat agttcctcct ttcagcaaaa aaccccctcaa gacccgttta gaggccccaa    60
ggggttatgc tagttattgc tcagcggtgg cagcagccaa ctcagcttcc tttcgggctt    120
tgttagcagc cggatctcag tggtggtggt ggtggtgctc gagtgcggcc gcaagctttt   180
acagatgcgt tttatcacac gatttcggtt ccactttttt gtccactttg gtattgctcg    240
gtttgtgatt gacgttgcag atatacgttt gggtacccag tgaggaactc ggaacggtaa    300
ccacgctgct caggctgtac aggcccgatg actgcagaac agccgggaac gtatgcacac    360
cagaggtcag tgcgccgctg ttccaggaga cggtaaccgg ttccggaaaa taatctttaa    420
ccagacaacc cagagctgcc gtaccgccac tggtagactt ggaactcggg ccagcgggaa    480
acacgctcgg gcctttggtg ctcgcgctgc tcacggtgac cagggtacct tggccccaaa    540
cgtcaaaata ccagtgggac gtgccatagt aatacgggta cttcgcgcag taatacacgg   600
cggtatcttc cgcgcgcaga ctgttcatct gcagatatgc cgtgctcttc gaggtgtcca    660
gagagaacgt aaagcgacgt ttaaaatcgg ccgcataggt cggttcaccc gtgtaggtat   720
taatccagcc cacccattcc agacctttac ccggggcctg acggacccag ttcataccat    780
aatgggtaaa atcatagccc gaggcagcac acgacagacg cagagagcca cccggttgga    840
ccagaccacc acccgattcg accagttgga cttcggccat cgccggctgg gcagcgagga    900
gcagcagacc agcagcagct gtcggcagca ggtatttcat atgtatatct ccttcttaaa    960
gttaaacaaa attatttcta gaggggaatt gttatccgct cacaattccc ctatagtgag    1020
tcgtattaat ttcgcgggat cgagatctttt atgacaactt gacggctaca tcattcactt    1080
tttcttcaca accggcacgg aactcgctcg gctggcccc ggtgcatttt ttaaataccc    1140
gcgagaaata gagttgatcg tcaaaaccaa cattgcgacc gacggtggcg ataggcatcc    1200
gggtggtgct caaaagcagc ttcgcctggc tgatacgttg gtcctcgcgc cagcttaaga    1260
cgctaatccc taactgctgg cggaaaagat gtgacagacg cgacggcgac aagcaaacat    1320
```

-continued

```
gctgtgcgac gctggcgata tcaaaattgc tgtctgccag gtgatcgctg atgtactgac    1380
aagcctcgcg tacccgatta tccatcggtg gatggagcga ctcgttaatc gcttccatgc    1440
gccgcagtaa caattgctca agcagattta tcgccagcag ctccgaatag cgcccttccc    1500
cttgcccggc gttaatgatt tgcccaaaca ggtcgctgaa atgcggctgg tgcgcttcat    1560
ccgggcgaaa gaaccccgta ttggcaaata ttgacggcca gttaagccat tcatgccagt    1620
aggcgcgcgg acgaaagtaa acccactggt gataccattc gcgagcctcc ggatgacgac    1680
cgtagtgatg aatctctcct ggcgggaaca gcaaaatatc acccggtcgg caaacaaatt    1740
ctcgtccctg attttccacc acccctgac cgcgaatggt gagattgaga atataacctt    1800
tcattcccag cggtcggtcg ataaaaaaat cgagataacc gttggcctca atcggcgtta    1860
aacccgccac cagatgggca ttaaacgagt atcccggcag caggggatca ttttgcgctt    1920
cagccatact tttcatactc ccgccattca gagaagaaac caattgtcca tattgcatca    1980
gacattgccg tcactgcgtc ttttactggc tcttctcgct aaccaaaccg gtaaccccgc    2040
ttattaaaag cattctgtaa caaagcggga ccaaagccat gacaaaaacg cgtaacaaaa    2100
gtgtctataa tcacggcaga aaagtccaca ttgattattt gcacggcgtc acactttgct    2160
atgccatagc atttttatcc ataagattag cggatcctac ctgacgcttt ttatcgcaac    2220
tctctactgt ttctccatac ccgtttttt gggctagaaa taattttgtt taactttaag    2280
aaggagatat acatatgaaa tacctgctgc cgacagctgc tgctggtctg ctgctcctcg    2340
ctgcccagcc ggcgatggcc gacattcaac tgacgcaaag tccgagcagc ctgagcgcat    2400
ccgtgggcga ccgtgtgacg attacctgtt ccgcaagcca agacatctct aactatctga    2460
attggtacca gcaaaaaccg ggcaaggcac cgaaagtcct gatttatttt accagctctc    2520
tgcattccgg cgttccgtca cgttttagcg gctctggtag tggcaccgat ttcaccctga    2580
cgatcagttc cctgcagccg gaagactttg ctacgtatta ctgccagcaa tacagcaccg    2640
tgccgtggac gttcggtcag ggcaccaagg ttgaaattaa acgtacggtt gcggcccgt    2700 ctgtctttat cttcccgccg agtgatgaac agctgaaatc gggtaccgca agcgtggttt    2760
gtctgctgaa caatttctat ccgcgcgaag caaaggtcca gtggaaagtg gacaacgctc    2820
tgcagtccgg caattcacaa gaatcggtga ccgaacaaga tagcaaggac tctacgtaca    2880
gtctgtcatc gaccctgacg ctgtccaaag cggattatga aaaacacaag gtttacgcct    2940
gcgaagtcac ccatcaaggt ctgtcgtctc cggttaccaa gagtttcaat cgtggcgaat    3000
gttaaaagct tggctgtttt ggcggatgag agaagatttt cagccgtgata cagattaaat    3060 cagaacgcag aagcggtctg ataaaacaga atttgcctgg cggcagtagc gcggtggtcc    3120
cacctgaccc catgccgaac tcagaagtga acgccgtag cgccgatggt agtgtggggt    3180
ctccccatgc gagagtaggg aactgccagg catcaaataa aacgaaaggc tcagtcgaaa    3240
gactgggcct ttcgttttat ctgttgtttg tcggtgaacg ctctcctgag taggacaaat    3300
ccgccgggag cggatttgaa cgttgcgaag caacggcccg gagggtggcg gcaggacgc    3360 ccgccataaa ctgccaggca tcaaattaag cagaaggcca tcctgacgga tggcctttt    3420 gcgtttctac aaactcttag atctcgatcc tctacgccgg acgcatcgtg gccggcatca    3480
ccggcgccac aggtgcggtt gctggcgcct atatcgccga catcaccgat ggggaagatc    3540
gggctcgcca cttcgggctc atgagcgctt gtttcggcgt gggtatggtg caggccccg    3600 tggccggggg actgttgggc gccatctcct tgcatgcacc attccttgcg gcggcggtgc    3660
tcaacggcct caacctacta ctgggctgct tcctaatgca ggagtcgcat aagggagagc    3720
```

-continued

```
gtcgagatcc cggacaccat cgaatggcgc aaaacctttc gcggtatggc atgatagcgc    3780
ccggaagaga gtcaattcag ggtggtgaat gtgaaaccag taacgttata cgatgtcgca    3840
gagtatgccg gtgtctctta tcagaccgtt tcccgcgtgg tgaaccaggc cagccacgtt    3900
tctgcgaaaa cgcgggaaaa agtggaagcg cgatggcgg agctgaatta cattcccaac     3960
cgcgtggcac aacaactggc gggcaaacag tcgttgctga ttggcgttgc cacctccagt    4020
ctggccctgc acgcgccgtc gcaaattgtc gcggcgatta atctcgcgc cgatcaactg     4080 ggtgccagcg tggtggtgtc gatggtagaa cgaagcggcg tcgaagcctg taaagcggcg    4140
gtgcacaatc ttctcgcgca acgcgtcagt gggctgatca ttaactatcc gctggatgac    4200
caggatgcca ttgctgtgga agctgcctgc actaatgttc cggcgttatt tcttgatgtc    4260
tctgaccaga cacccatcaa cagtattatt ttctcccatg aagacggtac gcgactgggc    4320
gtggagcatc tggtcgcatt gggtcaccag caaatcgcgc tgttagcggg cccattaagt    4380
tctgtctcgg cgcgtctgcg tctggctggc tggcataaat atctcactcg caatcaaatt    4440
cagccgatag cggaacggga aggcgactgg agtgccatgt ccggttttca acaaaccatg    4500
caaatgctga atgagggcat cgttcccact gcgatgctgg ttgccaacga tcagatggcg    4560
ctgggcgcaa tgcgcgccat taccgagtcc gggctgcgcg ttggtgcgga tatctcggta    4620
gtgggatacg acgataccga agacagctca tgttatatcc cgccgttaac caccatcaaa    4680
caggattttc gcctgctggg gcaaaccagc gtggaccgct tgctgcaact ctctcagggc    4740
caggcggtga agggcaatca gctgttgccc gtctcactgg tgaaaagaaa aaccaccctg    4800
gcgcccaata cgcaaaccgc ctctccccgc gcgttggccg attcattaat gcagctggca    4860
cgacaggttt cccgactgga aagcgggcag tgagcgcaac gcaattaatg taagttagct    4920
cactcattag gcaccgggat ctcgaccgat gcccttgaga gccttcaacc cagtcagctc    4980
cttccggtgg gcgcggggca tgactatcgt cgccgcactt atgactgtct tctttatcat    5040
gcaactcgta ggacaggtgc cggcagcgct ctgggtcatt ttcggcgagg accgctttcg    5100
ctggagcgcg acgatgatcg gcctgtcgct tgcggtattc ggaatcttgc acgccctcgc    5160
tcaagccttc gtcactggtc ccgccaccaa acgtttcggc gagaagcagg ccattatcgc    5220
cggcatggcg gccccacggg tgcgcatgat cgtgctcctg tcgttgagga cccggctagg    5280
ctggcggggt tgccttactg gttagcagaa tgaatcaccg atacgcgagc gaacgtgaag    5340
cgactgctgc tgcaaaacgt ctgcgacctg agcaacaaca tgaatggtct tcggtttccg    5400
tgtttcgtaa agtctggaaa cgcggaagtc agcgccctgc accattatgt tccggatctg    5460
catcgcagga tgctgctggc taccctgtgg aacacctaca tctgtattaa cgaagcgctg    5520
gcattgaccc tgagtgattt ttctctggtc ccgccgcatc cataccgcca gttgtttacc    5580
ctcacaacgt tccagtaacc gggcatgttc atcatcagta acccgtatcg tgagcatcct    5640
ctctcgtttc atcggtatca ttacccccat gaacagaaat ccccccttaca cggaggcatc    5700 agtgaccaaa caggaaaaaa ccgcccttaa catggcccgc tttatcagaa gccagacatt    5760
aacgcttctg gagaaactca acgagctgga cgcggatgaa caggcagaca tctgtgaatc    5820
gcttcacgac cacgctgatg agctttaccg cagctgcctc gcgcgtttcg gtgatgacgg    5880
tgaaaacctc tgacacatgc agctcccgga gacggtcaca gcttgtctgt aagcggatgc    5940
cgggagcaga caagcccgtc agggcgcgtc agcgggtgtt ggcgggtgtc ggggcgcagc    6000
catgacccag tcacgtagcg atagcggagt gtatactggc ttaactatgc ggcatcagag    6060
cagattgtac tgagagtgca ccatatatgc ggtgtgaaat accgcacaga tgcgtaagga    6120
```

```
gaaaataccg catcaggcgc tcttccgctt cctcgctcac tgactcgctg cgctcggtcg      6180
ttcggctgcg gcgagcggta tcagctcact caaaggcggt aatacggtta tccacagaat      6240
caggggataa cgcaggaaag aacatgtgag caaaaggcca gcaaaaggcc aggaaccgta      6300
aaaaggccgc gttgctggcg ttttccata ggctccgccc ccctgacgag catcacaaaa       6360
atcgacgctc aagtcagagg tggcgaaacc cgacaggact ataaagatac caggcgtttc      6420
cccctggaag ctccctcgtg cgctctcctg ttccgaccct gccgcttacc ggatacctgt      6480
ccgcctttct cccttcggga agcgtggcgc tttctcatag ctcacgctgt aggtatctca      6540
gttcggtgta ggtcgttcgc tccaagctgg gctgtgtgca cgaaccccc gttcagcccg       6600
accgctgcgc cttatccggt aactatcgtc ttgagtccaa cccggtaaga cacgacttat      6660
cgccactggc agcagccact ggtaacagga ttagcagagc gaggtatgta ggcggtgcta      6720
cagagttctt gaagtggtgg cctaactacg gctacactag aaggacagta tttggtatct      6780
gcgctctgct gaagccagtt accttcggaa aaagagttgg tagctcttga tccggcaaac      6840
aaaccaccgc tggtagcggt ggtttttttg tttgcaagca gcagattacg cgcagaaaaa      6900
aaggatctca agaagatcct ttgatctttt ctacggggtc tgacgctcag tggaacgaaa      6960
actcacgtta agggattttg gtcatgagat tatcaaaaag gatcttcacc tagatccttt      7020
taaattaaaa atgaagtttt aaatcaatct aaagtatata tgagtaaact tggtctgaca      7080
gttaccaatg cttaatcagt gaggcaccta tctcagcgat ctgtctattt cgttcatcca      7140
tagttgcctg actccccgtc gtgtagataa ctacgatacg ggagggctta ccatctggcc      7200
ccagtgctgc aatgataccg cgagacccac gctcaccggc tccagattta tcagcaataa      7260
accagccagc cggaagggcc gagcgcagaa gtggtcctgc aactttatcc gcctccatcc      7320
agtctattaa ttgttgccgg gaagctagag taagtagttc gccagttaat agtttgcgca      7380
acgttgttgc cattgctgca ggcatcgtgg tgtcacgctc gtcgtttggt atggcttcat      7440
tcagctccgg ttcccaacga tcaaggcgag ttacatgatc ccccatgttg tgcaaaaaag      7500
cggttagctc cttcggtcct ccgatcgttg tcagaagtaa gttggccgca gtgttatcac      7560
tcatggttat ggcagcactg cataattctc ttactgtcat gccatccgta agatgctttt      7620
ctgtgactgg tgagtactca accaagtcat tctgagaata gtgtatgcgg cgaccgagtt      7680
gctcttgccc ggcgtcaata cgggataata ccgcgccaca tagcagaact ttaaaagtgc      7740
tcatcattgg aaaacgttct tcggggcgaa aactctcaag gatcttaccg ctgttgagat      7800
ccagttcgat gtaacccact cgtgcaccca actgatcttc agcatctttt actttcacca      7860
gcgtttctgg gtgagcaaaa acaggaaggc aaaatgccgc aaaaaaggga ataagggcga      7920
cacggaaatg ttgaatactc atactcttcc tttttcaata ttattgaagc atttatcagg      7980
gttattgtct catgagcgga tacatatttg aatgtattta gaaaaataaa caaatagggg      8040
ttccgcgcac atttccccga aaagtgccac ctgaaattgt aaacgttaat attttgttaa      8100
aattcgcgtt aaattttgt taaatcagct catttttaa ccaataggcc gaaatcggca       8160
aaatccctta taaatcaaaa gaatagaccg agatagggtt gagtgttgtt ccagtttgga      8220
acaagagtcc actattaaag aacgtggact ccaacgtcaa agggcgaaaa accgtctatc      8280
agggcgatgg cccactacgt gaaccatcac cctaatcaag ttttttgggg tcgaggtgcc      8340
gtaaagcact aaatcggaac cctaaaggga gcccccgatt tagagcttga cggggaaagc      8400
cggcgaacgt ggcgagaaag gaagggaaga aagcgaaagg agcgggcgct agggcgctgg      8460
```

```
caagtgtagc ggtcacgctg cgcgtaacca ccacaccegc cgcgcttaat gcgccgctac    8520
agggcgcgtc ccattcgcca                                                8540
```